(12) United States Patent
Lainay et al.

(10) Patent No.: US 8,872,512 B2
(45) Date of Patent: Oct. 28, 2014

(54) BENCH AND A METHOD FOR MAGNETOSCOPICALLY TESTING A TURBINE ENGINE SHAFT

(75) Inventors: Guillaume Lainay, Moissy Cramayel Cedex (FR); Jean-Claude Lemoal, Moissy Cramayel Cedex (FR); Lionel Thierry, Moissy Cramayel Cedex (FR)

(73) Assignee: SNECMA, Paris (FR)

( * ) Notice: Subject to any disclaimer, the term of this patent is extended or adjusted under 35 U.S.C. 154(b) by 314 days.

(21) Appl. No.: 13/377,019

(22) PCT Filed: Jun. 8, 2010

(86) PCT No.: PCT/FR2010/051138
§ 371 (c)(1),
(2), (4) Date: Dec. 8, 2011

(87) PCT Pub. No.: WO2010/142911
PCT Pub. Date: Dec. 16, 2010

(65) Prior Publication Data
US 2012/0086441 A1    Apr. 12, 2012

(30) Foreign Application Priority Data
Jun. 10, 2009    (FR) ...................................... 09 02815

(51) Int. Cl.
*G01N 27/84*    (2006.01)
(52) U.S. Cl.
CPC ..................... *G01N 27/84* (2013.01)
USPC ........................................................ 324/216
(58) Field of Classification Search
None
See application file for complete search history.

(56) References Cited

U.S. PATENT DOCUMENTS

| | | | | |
|---|---|---|---|---|
| 2,682,032 A | * | 6/1954 | Dehn et al. ..................... | 324/216 |
| 3,480,855 A | * | 11/1969 | Lorenzi ......................... | 324/216 |
| 5,424,639 A | | 6/1995 | Meiffren et al. | |
| 7,107,863 B2 | * | 9/2006 | Harthorn et al. ............. | 73/865.8 |
| 2005/0200842 A1 | | 9/2005 | Bonningue et al. | |
| 2008/0297785 A1 | | 12/2008 | Bonningue et al. | |

FOREIGN PATENT DOCUMENTS

| | | |
|---|---|---|
| EP | 0 593 357 | 4/1994 |
| EP | 1 494 060 | 1/2005 |
| FR | 2 920 537 | 3/2009 |
| GB | 2 413 854 | 11/2005 |
| JP | 4 332995 | 12/1993 |

OTHER PUBLICATIONS

International Search Report Issued Nov. 12, 2010 in PCT/FR10/51138 Filed Jun. 8. 2010.

* cited by examiner

*Primary Examiner* — Paresh Patel
(74) *Attorney, Agent, or Firm* — Oblon, Spivak, McClelland, Maier & Neustadt, L.L.P.

(57) ABSTRACT

A bench for magnetoscopically testing a tubular part, the bench including a tool of elongate shape for inserting inside the part and carrying an endoscopic mechanism for ultraviolet illumination of the inside surface of the part and for observing any defects of the part, and an indexing mechanism co-operating by mutual engagement with external references of the tool that are regularly distributed over at least a fraction of its length to control accurately the advance and the position of the tool inside the part.

13 Claims, 1 Drawing Sheet

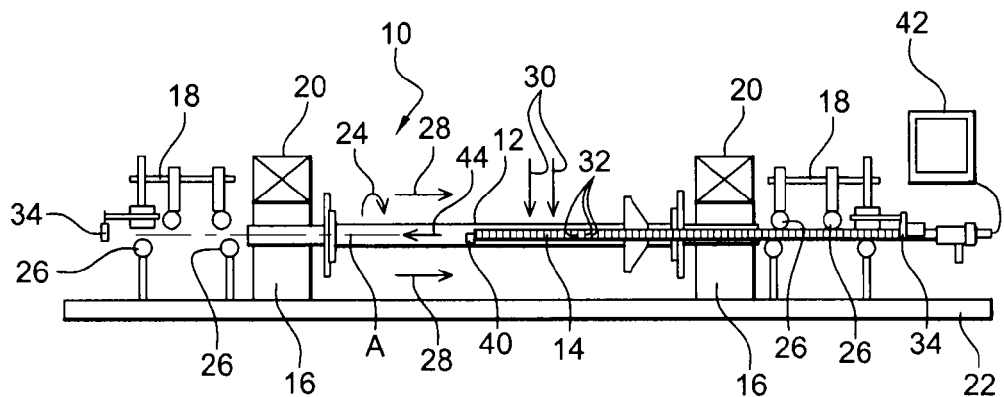
Fig. 1
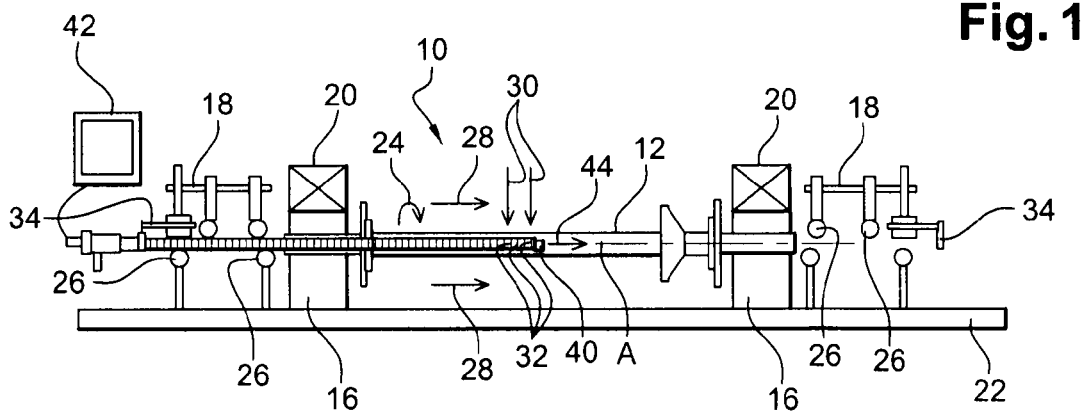
Fig. 2
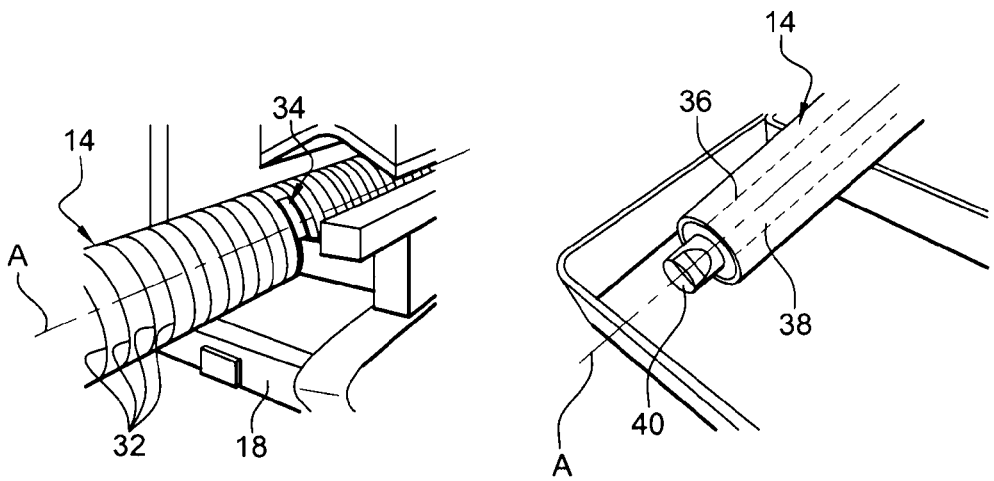
Fig. 3                     Fig. 4

BENCH AND A METHOD FOR MAGNETOSCOPICALLY TESTING A TURBINE ENGINE SHAFT

BACKGROUND OF THE INVENTION

1 Field of the Invention

The present invention relates to a bench and a method for magnetoscopically testing a tubular part such as a turbine engine shaft.

2 Discussion of the Background

Magnetoscopic testing (MT) is a technique for non-destructive testing (NDT) that makes it possible to detect defects in the surface of a part made of ferromagnetic material, or inside said material. This technique consists in spraying a substance containing colored particles or ferromagnetic particles coated in a fluorescent pigment onto the surface of the part that is to be tested, and then in subjecting the part to a magnetic field, while endoscopically observing under white light or ultraviolet light the surface that has been treated with the substance.

When the current lines of the magnetic field encounter a defect in the part, they are deflected, thereby creating a leakage field at the surface of the part that attracts the ferromagnetic particles in register with the defects, these particles being observable under ultraviolet lighting because of the presence of the fluorescent pigment.

Low pressure turbine and low pressure compressor shafts of a turbine engine need to be magnetoscopically tested after being fabricated in order to detect any metallurgical defects such as inclusions or machining cracks, and also during maintenance operations in order to detect any cracks due to operation of the engine. Such shafts are tubular and their entire inside and outside surfaces need to be subjected to magnetoscopic testing.

At present, observing the cylindrical inside surface of a turbine engine shaft under ultraviolet light is performed by means of a stick that is designed to be engaged into the shaft via one of its ends and that carries at its distal end a source of ultraviolet light together with an inclined mirror for reflecting images to a charged-coupled device (CCD) camera situated at the proximal end of the stick.

That technology presents numerous drawbacks. The stick carries equipment that is relatively complex and bulky. The ultraviolet light source is formed by neon lamps that do not enable the inside surface of the shaft to be illuminated uniformly, and that emit light at a wavelength that is difficult to control, which means that it is not possible to achieve good observation conditions. Furthermore, because of its size and its shape, the mirror reflects images of small size, thereby making it difficult to detect defects. Finally, the stick is moved in translation inside the shaft at the same time as the shaft is being rotated about its axis, thereby leading to the inside surface of the shaft being scanned helically by the lighting spot defined by the endoscopic means, giving rise to deformation of the images recorded by the camera. It is also difficult under such circumstances to obtain sufficient overlap of the inspected surfaces so as to guarantee that the entire inside surface of the shaft has been inspected.

SUMMARY OF THE INVENTION

A particular object of the invention is to provide a solution to those problems that is simple, effective, and inexpensive.

To this end, the invention provides a bench for magnetoscopic testing of a tubular part such as a turbine engine shaft, the bench comprising means for supporting the part and for turning it, a tool of elongate shape carrying endoscopic means for ultraviolet illumination of the inside surface of the part and for observing any defects in the part, and means for supporting and guiding the tool to move in translation so as to be inserted inside the part, the bench being characterized in that the tool includes a plurality of external references that are regularly distributed over at least a fraction of its length and that define regular steps for advancing the tool in translation along the longitudinal axis of the part, the means for supporting and guiding the tool including indexing means that co-operate with the references of the tool by mutual engagement in order to control accurately the advance and the position of the tool in the part.

According to the invention, the external references of the tool for supporting the endoscopic means make it possible to determine accurately the position of the tool inside the part under test, and thus to determine which zone of the part is being observed with the help of the endoscopic means. These references distributed along the tool define incremental regular advance steps for moving the tool in translation inside the part. The tool is designed to be held in axial position inside the part while the part is rotated about its axis. This enables an annular zone to be scanned inside the part with the lighting spot of the endoscopic means of the tool. Once the annular zone has been inspected in full, the tool is advanced or reversed through one step inside the part in order to inspect a new annular zone that overlaps the above-mentioned annular zone, at least in part. These operations are repeated in order to inspect the entire inside surface of the part. The tool of the invention is thus designed to be moved stepwise inside the part for inspection. Not turning the part under test while the tool is being moved serves to limit deformation of the images picked up by the endoscopic means of the tool.

The tool of the invention may be manipulated by hand by a person, or else in automatic manner. The external references of the tool may be annular references extending around the longitudinal axis of the tool. They are formed by applying annular marks or by forming annular grooves to the outside surface of the tool. The distance between two references may be about 1 centimeter (cm).

The tool of the invention may be generally cylindrical in shape and it is advantageously tubular, with the endoscopic means being housed inside the tool and extending therealong. This makes it possible to protect the endoscopic means and to limit the overall size of the tool. Furthermore, the tool is rigid, thereby preventing the endoscopic means from flexing and vibrating while in use.

The endoscopic means may comprise ultraviolet light guide means and image transmission means, which means extend from the proximal end of the tool to its distal end, and project axially from said distal end.

Advantageously, the image transmission means include at least one prism at their distal end. The use of such a prism guarantees good quality image transmission.

According to another characteristic of the invention, each advance step of the tool has a size that is equal to or less than the diameter of the observation field of the endoscopic means. Preferably, each step has a size that is substantially equal to half the diameter of the observation field of the endoscopic means.

The bench of the invention may include means for supporting and guiding the tool at each of the ends of the part in order to insert the tool into the part via one or the other of its ends.

When the part for testing is of great length, the tool is engaged in the part via one of its ends, and then via its other end, so as to inspect the entire inside surface of the part.

The means for supporting and guiding the tool include indexing means that co-operate by mutual engagement with the external references of the tool in order to control accurately the advance and the position of the tool inside the part.

Finally, the invention provides a method of magnetoscopically testing a tubular part by means of a bench as described above, the method being characterized in that it comprises the steps consisting in:

a) inserting the tool in the part for testing via one of its ends until it occupies a desired position in said part, said position being defined by indexing means of the bench co-operating by mutual engagement with references of the tool;

b) holding the tool stationary and turning the part about its axis in order to inspect an annular zone inside the part with the help of the endoscopic means of the tool;

c) then moving the tool inside the part through one step in a longitudinal direction until the indexing means co-operate by mutual engagement with an adjacent reference of the tool; and d) repeating steps b) and c) until the part has been inspected over a desired length.

The method also consists in repeating steps a), b), c), and d) by inserting the tool into the other end of the part.

The method of the invention may further consist in inspecting each part twice, the part being subjected to a longitudinal magnetic field during the first inspection and to a transverse magnetic field during the second inspection.

Defects in the part are best detected when the field lines of the magnetic field are perpendicular to the defects. Applying a longitudinal magnetic field to the part serves to detect defects in the part that are oriented substantially circumferentially, whereas applying a transverse magnetic field to the part serves to detect defects in the part having an orientation that is substantially axial.

BRIEF DESCRIPTION OF THE DRAWINGS

The invention can be better understood and other details, characteristics, and advantages of the present invention appear more clearly on reading the following description of non-limiting examples described with reference to the accompanying drawings, in which:

DETAILED DESCRIPTION OF THE PREFERRED EMBODIMENTS

FIGS. 1 and 2 are diagrammatic views of a bench of the invention for non-destructive testing by magnetoscopy, and they show two steps of the testing method of the invention; and FIGS. 3 and 4 are fragmentary diagrammatic views in perspective of the tool of the invention for magnetoscopic testing of a tubular part.

Reference is made initially to FIG. 1, which shows a bench 10 for non-destructive testing (NDT) by magnetoscopy of a tubular part that, in the example shown, is constituted by a turbine engine shaft 12, and in particular a low pressure turbine or low pressure compressor shaft of a turbine engine.

The shaft 12 is generally cylindrical and elongate in shape about a longitudinal axis A, and it is made of a ferromagnetic material. The inside and outside cylindrical surfaces of the shaft 12 need to be tested magnetoscopically after the shaft has been fabricated or during maintenance operations on the turbine engine in order to detect the presence of potential defects in the ferromagnetic material of the shaft.

Magnetoscopic testing of the inside surface of the shaft 12 is essentially performed in two steps: a first step in which a substance containing ferromagnetic particles coated in a fluorescent pigment is sprayed onto the inside surface of the shaft, and a second step in which the shaft is subjected to a magnetic field while a tool 14 carrying endoscopic means is engaged inside the shaft to visually inspect, under ultraviolet lighting, the inside surface thereof that has been treated with the above-mentioned substance.

The test bench 10 includes means 16 for supporting the shaft 12 and for turning it about its axis A, a non-destructive magnetoscopic test tool 14 of the above-mentioned type, means 18 for supporting and guiding the tool to move in translation inside the shaft 12, and magnetic field generator means 20.

The shaft 12 is held at each of its ends by support means 16 that are fastened to the floor 22. These support means 16 enable the shaft 12 to be turned about its axis A (arrow 24).

Means for supporting the tool 14 are arranged at each end of the shaft 12 so that the tool can be engaged and guided through one or other of the ends of the shaft, as can be seen in FIGS. 1 and 2. By way of example, these support means 18 comprise wheels 26 for guiding the tool to move in axial translation inside the shaft in a horizontal plane.

The magnetic field generators 20 are suitable for applying a magnetic field to the shaft 12 in a longitudinal direction (arrows 28) and/or in a transverse direction (arrows 30).

The tool 14 of the invention includes endoscopic means housed inside a tubular cylindrical body that has references 32 formed on the outside surface thereof to define a regular pitch for advancing the tool in translation along the axis A of the shaft.

In the example shown, these references 32 are constituted by external annular marks or by external annular grooves extending around the longitudinal axis of the tool (FIGS. 1 to 3). These references 32 are formed on a major fraction of the length of the body of the tool.

The means 18 for supporting the tool 14 are fitted with indexing means 34 that co-operate with the references 32 of the tool to control and determine accurately the axial position of the tool in the shaft 12. In the example shown in FIG. 3, these indexing means are of the ball type, e.g. co-operating with the annular groove 32 of the tool by mutual engagement, thereby holding the tool in an axial position relative to the shaft 12.

The endoscopic means carried by the tool 14 comprise image transmission means 36 and ultraviolet light guide means 38 that extend axially inside the body of the tool.

The image transmission means 36 project axially from the distal end of the body of the tool (FIG. 4) and, at said end, they comprise at least one prism 40 for reflecting images towards a series of lenses or the like housed in the body of the tool. By way of example, the images are captured by a camera situated at the proximal end of the tool so as to be subsequently viewed on a monitor screen. In a variant, the image transmission means 36 include an eyepiece at their proximal end.

The light guide means 38 are connected at the proximal end of the tool to a source of ultraviolet light and they project axially at their opposite end from the distal end of the body of the tool.

The endoscopic means are of the deflected distal aiming type, i.e. the observation axis defined by the prism of the image transmission means 36 is oriented laterally, substantially perpendicularly to the longitudinal axis of the tool, and the aiming axis defined by the distal end of the light guide means 38 is substantially parallel to said aiming axis.

The means 36, 38 for transmitting images and guiding light are also connected at their proximal ends to a control and data processor unit 42.

The light spot defined by the lighting means of the endoscopic means is generally circular in shape. The tool 14 is designed to be engaged in the shaft via one of its ends (FIG. 1) and to be held in a given axial position inside the shaft with the help of the indexing means 34. The tool is held stationary by the support means 18 while the shaft 12 is turned about its axis A by the support means 16 (arrow 24) so that the lighting spot of the endoscopic means of the tool scan an inside annular surface of the shaft. The tool is then moved in translation through one step forwards or rearwards inside the shaft (arrow 42), and is then held stationary once more by the indexing means 34 of the support means 18. Turning the shaft 12 then causes the lighting spot of the endoscopic means to scan a new internal annular surface of the shaft, which surface overlaps at least in part the previously inspected annular surface. The tool 14 is thus moved forwards or rearwards in steps inside the shaft and is held stationary after each such movement while the shaft 12 is being turned.

When each movement step of the tool presents a dimension that is equal to substantially half the diameter of the lighting spot of the endoscopic means, each annular surface inspected by the lighting spot covers half of each of the adjacent inspected annular surfaces, thereby enabling the entire inside surface of the shaft to be inspected twice.

When the shaft 12 for inspection is of great length and its inside surface cannot be inspected in full by engaging the tool through only one of its ends, the tool is engaged initially into the shaft via one of its ends in order to inspect a first half of its inside surface (FIG. 1), and is then engaged again into the shaft via its other end in order to inspect the second half of its inside surface (FIG. 2).

The above-mentioned steps of the method of the invention as shown in FIGS. 1 and 2 are performed while subjecting the shaft to a magnetic field in the longitudinal direction (arrows 28) in order to detect shaft defects that are oriented substantially circumferentially, the steps are then repeated while subjecting the shaft to a magnetic field in a transverse direction (arrows 30) in order to detect shaft defects that are oriented in a substantially axial direction.

The tool 14 may be moved and the shaft 12 may be turned either manually or automatically.

The shaft 12 may have a length lying in the range about 1.8 meters (m) to about 2 m, and the tool 14 may have a length of about 1.8 m. The tool 14 may present a section that is circular, square, polygonal, or arbitrary in shape. The step size defined by the external references 32 on the tool may be about 10 millimeters (mm).

The invention claimed is:

1. A bench for magnetoscopic testing of a tubular part, the bench comprising:
   means for supporting the part and for turning the part;
   a tool of elongate shape carrying endoscopic means for ultraviolet illumination of an inside surface of the part and for observing any defects in the part; and
   means for supporting and guiding the tool to move in translation so as to be inserted inside the part, wherein the tool includes a plurality of external references that are regularly distributed over at least a fraction of its length and that define regular steps for advancing the tool in translation along the longitudinal axis of the part, the means for supporting and guiding the tool including indexing means that co-operate with the references of the tool by mutual engagement to control accurately an advance and a position of the tool in the part.

2. A bench according to claim 1, wherein the tool includes a plurality of annular references extending around the longitudinal axis of the tool.

3. A bench according to claim 2, wherein the annular references are formed by applying annular marks or by forming annular grooves to an outside surface of the tool.

4. A bench according to claim 1, wherein the tool is generally cylindrical in shape.

5. A bench according to claim 1, wherein the tool is tubular and the endoscopic means extends inside the tool.

6. A bench according to claim 1, wherein the endoscopic means comprises ultraviolet light guide means and image transmission means, which image transmission means extend from a proximal end of the tool to its distal end, and project axially from the distal end.

7. A bench according to claim 6, wherein the image transmission means includes at least one prism at its distal end.

8. A bench according to claim 1, wherein each advance step is of a size that is equal to or less than the diameter of an observation field of the endoscopic means.

9. A bench according to claim 1, wherein each advance step is of a size equal to half the diameter of an observation field of the endoscopic means.

10. A bench according to claim 1, further comprising means for supporting and guiding the tool at each of ends of the part to insert the tool into the part via one or the other of its ends.

11. A method of magnetoscopically testing a tubular part by a bench according to claim 1, the method comprising:
   a) inserting the tool in the part via one of its ends until it occupies a desired position in the part, the position being defined by indexing means of the bench co-operating by mutual engagement with references of the tool;
   b) holding the tool stationary and turning the part about its axis to inspect an annular zone inside the part with help of the endoscopic means of the tool;
   c) then moving the tool inside the part through one step in a longitudinal direction until the indexing means co-operates by mutual engagement with an adjacent reference of the tool; and
   d) repeating b) and c) until the inside of the part has been inspected over a desired length.

12. A method according to claim 11, further comprising repeating a), b), c), and d) by inserting the tool into the other end of the part.

13. A method according to claim 1, further comprising inspecting each part twice, the part being subjected to a longitudinal magnetic field during a first inspection and to a transverse magnetic field during a second inspection.

* * * * *